US011389554B2

(12) United States Patent
Lee

(10) Patent No.: US 11,389,554 B2
(45) Date of Patent: Jul. 19, 2022

(54) UV-C STERILIZER ATTACHABLE TO TOUCH SCREEN OF AUTOMATED MACHINE

(71) Applicant: HADELSYS CO., LTD., Siheung-si (KR)

(72) Inventor: Won Gee Lee, Seoul (KR)

(73) Assignee: HADELSYS CO., LTD., Gyeonggi-Do (KR)

( * ) Notice: Subject to any disclaimer, the term of this patent is extended or adjusted under 35 U.S.C. 154(b) by 257 days.

(21) Appl. No.: 16/911,908

(22) Filed: Jun. 25, 2020

(65) Prior Publication Data

US 2021/0369885 A1    Dec. 2, 2021

(30) Foreign Application Priority Data

May 28, 2020    (KR) .......................... 10-2020-0064063

(51) Int. Cl.
*A61L 2/10*     (2006.01)
*A61L 2/24*     (2006.01)
(Continued)

(52) U.S. Cl.
CPC ....... *A61L 2/10* (2013.01); *A61L 2/24* (2013.01); *A61L 2/26* (2013.01); *G07F 19/201* (2013.01);
(Continued)

(58) Field of Classification Search
CPC ..... A61L 2/10; A61L 2/24; A61L 2/26; A61L 2202/11; A61L 2202/121; A61L 2202/14;
(Continued)

(56) References Cited

U.S. PATENT DOCUMENTS

| 9,912,790 B2* | 3/2018 | Kim .......................... A61L 2/10 |
| 10,596,281 B1 | 3/2020 | Tchon et al. |
| 2015/0174276 A1 | 6/2015 | Tumanov |

FOREIGN PATENT DOCUMENTS

| JP | 2002142737 | 5/2002 |
| KR | 2020110002728 | 3/2011 |

(Continued)

OTHER PUBLICATIONS

Kim, et al., UVC LED Irradiation Effectively Inactivates Aerosolized Viruses, Bacteria, and Fungi in a Chamber-Type Air Disinfection System, Applied and Environmental Microbiology, Sep. 2018, vol. 84, Issue 17, pp. 1-11, American Society for Microbiology.

(Continued)

*Primary Examiner* — Bao Q Truong
(74) *Attorney, Agent, or Firm* — Cantor Colburn LLP

(57) ABSTRACT

Provided is a sterilizer which is simply attached to the bezel of a touch screen of the existing automated machine (an ATM, a kiosk, or a vending machine, etc.), and sterilizes the surface of the touch screen by vertically moving the moving UV bar (20) having UV-C light source by using a driving means. The sterilizer includes: a base plate (10) having an open portion (11) corresponding to the touch screen (2) of an automated machine (1) and attachable to a bezel of the touch screen (2); a moving UV bar (20) having a light source (21), and a protection cover (22) preventing light of the light source from being emitted in directions other than a direction toward a surface of a touch screen; and a horizontal cover (14) provided in a horizontal direction under the open portion, and a vertical cover (13L, 13R).

4 Claims, 12 Drawing Sheets

(51) Int. Cl.
*A61L 2/26* (2006.01)
*G07F 19/00* (2006.01)

(52) U.S. Cl.
CPC ...... *A61L 2202/11* (2013.01); *A61L 2202/121* (2013.01); *A61L 2202/14* (2013.01)

(58) Field of Classification Search
CPC ...... A61L 2202/16; A61L 2/08; A61L 2/0029; A61L 2/00; A61L 2/0047; A61L 2202/00; A61L 2202/10; G07F 19/201
See application file for complete search history.

(56) References Cited

FOREIGN PATENT DOCUMENTS

| | | |
|---|---|---|
| KR | 20110089385 | 8/2011 |
| KR | 101132762 | 4/2012 |
| KR | 101158046 | 6/2012 |
| KR | 20120129453 | 11/2012 |

OTHER PUBLICATIONS

Welch, et al., Far-UVC light: A new tool to control the spread of airborne-mediated microbial diseases, Scientific Reports, 2018, pp. 1-7.

\* cited by examiner

UV-C STERILIZER ATTACHABLE TO TOUCH SCREEN OF AUTOMATED MACHINE

BACKGROUND OF THE INVENTION

Field of the Invention

The present invention relates generally to a sterilizer attachable to an input pad of an ATM, a kiosk, or a vending machine, etc. More particularly, the present invention relates to a sterilizer attachable to the input pad of an automated machine (an ATM, a kiosk, a vending machine, etc.) which is currently used in many places for various purposes, particularly, to the bezel of a touch screen of the automated machine without being embedded in a newly manufactured automated machine (an ATM, a kiosk, or a vending machine, etc.).

Description of the Related Art

Recently, a vending machine, through which a user can directly order or purchase goods without the help of a salesperson, is used in various fields. There are many types of vending machines, such as ATMs for financial transactions, kiosks through which consumers receive services or goods which they want to buy after paying for the services or goods at theaters or markets, and vending machines, through which you can buy drinks or cigarettes. Hereinafter, such machines are referred to as "automated machines".

All such automated machines have an input pad, through which a desired service or item is selected and various information required for ordering is input. The input pad may be a button or a touch screen.

Automated machines are used by a large number of people, and it is very likely that bacteria or viruses get on the input pad of each of the automated machines touched by many users, so these bacteria can reproduce on the surface of the input pad or spread to the next users.

In particular, there is a high risk that many influenza viruses or bacteria, including the recently spreading coronavirus (COVID-19), will infect numerous users through the input pad of the automated machine. "Automated machines" mentioned in the present invention include an elevator provided with the input pad.

A number of conventional arts for removing viruses and bacteria by emitting a predetermined amount of ultraviolet light on the surface of the input pad of a keyboard, a smartphone, an ATM, or a kiosk have been disclosed.

Although the ability of UV-C's to remove viruses is well known, UV-C should not be exposed to human skin or eyes because it is known to cause carcinogenesis and cataracts in mammals. However, it is known that UV-C having a specific wavelength (207 to 222 nm) among UV-C can efficiently remove viruses without harming mammalian skin. However, it is clear that LEDs emitting UV-C having this specific wavelength (207 to 222 nm) have not been developed yet, and will be very expensive even if developed in the near future.

Therefore, it is necessary to use a UV-C LED emitting the light of a wavelength of 265 to 280 nm, which is known to have the best sterilization effect, but the UV-C LED is required to be developed in a structure in which UV-C is prevented from being emitted on the human body (particularly, the eyes and hands).

In the process in which a sterilizer attached to the automated machine normally operates, UV-C light is required to be prevented from being emitted on a portion (for example, the fingers, the face, or the eyes, etc.) of the body of a user, and to be emitted to be focused only on a target (the surface of the input pad) to be sterilized so that the operation time of the sterilizer is minimized and sterilization efficiency is maximized. In addition, measures to protect a user who does an abnormal action (for example, the action of pushing the fingers between the UV-C light source and the surface of the input pad) from UV-C should also be considered.

Furthermore, from a point of view, it is preferable that a UV-C sterilizer is configured to be embedded inside the casing of the automated machine (an ATM, a kiosk, a vending machine, etc.). However, since the automated machine (an ATM, a kiosk, a vending machine, etc.) is used in many places for various purposes, a sterilizer having a simple structure capable of sterilizing the surface of the input pad by being simply attached to the bezel of the input pad of the existing automated machine without replacing the automated machine is required.

Furthermore, since a touch screen as an embodiment of the input pad may receive information from a user or provide information to the user, many automated machines are provided with the touch screen instead of having multiple buttons.

However, since the area of the touch screen is generally larger than the area of the button-type input pad, a method of maximizing sterilization efficiency while minimizing transaction time for sterilizing is required.

DOCUMENTS OF RELATED ART (Patent Document 1) Korean Utility Model Application Publication No. 20-2011-0002728;
(Patent Document 2) Korean Patent No. 10-1158046;
(Patent Document 3) Korean Patent Application Publication No. 10-2011-0089385;
(Patent Document 4) Korean Patent No. 10-1132762;
(Patent Document 5) U.S. Pat. No. 10,596,281; and
(Patent Document 6) US Patent Application Publication No. 2015/0174276

NON-PATENT DOCUMENTS (Non-patent Document 1) American Society Microbiology "UVC LED irradiation effectively inactivates aerosolized viruses, bacteria, and fungi in a chamber-type air disinfection system" (Published 29 Jun. 2018), and
(Non-patent Document 2) Nature, Scientific Reports "Far-UVC light: A new tool to control the spread of airborne-mediated microbial diseases" (Published 9 Feb. 2018).

SUMMARY OF THE INVENTION

Accordingly, the present invention has been made keeping in mind the above problems occurring in the related art, and the present invention is intended to propose a UV-C sterilizer which is simply attached to the bezel of a touch screen of an automated machine.

The present invention is further intended to propose a UV-C sterilizer that can protect a user from UV-C light while sterilizing an input pad of an automated machine by irradiating the surface of the touch screen of the automated machine with UV-C light of a wavelength range harmful to the human body The present invention is still further intended to propose a sterilizer that in the case that many people are waiting to use an automated machine, allows a sterilization operation to be completed during a short time when a next user approaches the automated machine after a previous user finishes using the automated machine so that the next user does not wait during time required to sterilize the touch screen, thereby minimizing transaction time for sterilizing and maximizing sterilization efficiency.

The present invention is still further intended to provide a sterilizer having high durability that is not easily broken by abnormal manipulation or external forces.

In order to achieve the above objectives, according to one aspect of the present invention, there is provided a sterilizer including: a base plate having an open portion corresponding to a touch screen of an automated machine and attachable to a bezel of the touch screen; a moving UV bar having a light source emitting UV-C toward the open portion of the base plate and vertically moving; a drive source vertically moving the moving UV bar; and a driving means provided at each of left and right opposite ends of the moving UV bar and vertically moving the left and right opposite ends of the moving UV bar by receiving power from the drive source.

In the sterilizing device of the present invention configured as described above, the moving UV bar may sterilize the surface of the touch screen located at the open portion by emitting UV-C toward the open portion of the base plate while the moving UV bar moves up and down in close to the surface of the touch screen.

The sterilizer of the present invention may further include a horizontal cover provided in a horizontal direction above or under the open portion, and a vertical cover provided at each of opposite sides of the open portion to protect the driving means. The horizontal cover according to an embodiment of the present invention may be provided in the horizontal direction under the open portion.

The moving UV bar of the sterilizer according to the embodiment of the present invention may include the light source in which multiple high-power UV-C LEDs are integrated to the longitudinal bar, and a protection cover preventing light of the light source from being emitted in directions other than a direction toward a surface of the touch screen.

In the sterilizer according to the embodiment of the present invention, a gap defined between the lower edge of the protection cover and the surface of the touch screen may be configured to be narrow to prevent the finger of a user from entering the gap. Particularly, in the sterilizer according to the embodiment of the present invention, the moving UV bar may be configured to move in directions away from and toward the surface of a sterilization target by corresponding to the change of height of the surface (for example, the surface of the bezel of the touch screen protrudes more than the surface of the touch screen) of a sterilization target, which changes in height, while the moving UV bar moves up and down along the surface of a sterilization target, so that a predetermined gap to prevent the finger of a user from entering the gap defined between the lower edge of the protection cover and the surface of a sterilization target is maintained.

To protect a user, the sterilizer according to the embodiment of the present invention may further include a controller receiving information on whether or not a user is in front of the automated machine from the automated machine, and controlling such that the sterilizer is operated when there is no user.

The controller may be configured to control the sterilizer such that an electric current is applied to the UV-C LEDs only when each part of a driving mechanism, a control board, and a software is recognized to be in a normal state.

The controller may be configured to control the sterilizer such that a status result value of the sterilizer is transmitted to the automated machine after checking whether each part thereof is in a normal state such that information on whether the sterilizer is operated or the maintenance of the sterilizer can be maintained inside the operating system of the entirety of the automated machine.

The sterilizer according to the embodiment of the present invention includes the light source in which the multiple high-power UV-C LEDs are arranged at predetermined intervals on a longitudinal bar and integrated thereto, and allows a distance defined between the light source and the surface of a sterilization target to be optimized, so that a rapid moving speed of the light source is secured and a high sterilization effect is maintained.

In the sterilizer according to the embodiment of the present invention, to compactly provide the driving means inside space defined by the covers and the base plate, and to stably embody the vertical movement of the moving UV bar, a drive pulley rotated by receiving the rotational force of a drive motor may be provided at each of left and right sides of the base plate; a driven pulley and a timing belt corresponding to the drive pulley may be provided at each of the left and right sides; and the opposite ends of the moving UV bar are coupled to the timing belts, so that the moving UV bar is moved up and down by the movement of the timing belts.

The driving means of the sterilizer according to the embodiment of the present invention may further include a torque limiter preventing damage of components of the automated machine when the movement of the moving UV bar is restricted by impact of a user while the moving UV bar performs UV-C sterilization during the vertical movement. In the sterilizer having the torque limiter, the torque limiter may control so that the moving UV bar is returned to an original position thereof or is moved to a temporary position after a user determines that an operational malfunction occurs when the moving UV bar does not reach a sensor at a specific position by a predetermined time.

Other problems to be solved by the sterilizer according to the present invention and specific means for solving the problems will be described in more detail in the detailed description of the present invention to be described hereinafter.

The UV-C sterilizer according to the present invention is a compact sterilizer, wherein the driving means is compactly provided inside the vertical covers 13L and 13R of the opposite sides of the open portion in the center of the base plate relative thereto and the horizontal cover 14 above or under the open portion. The sterilizer can be used simply by being attached to the bezel of the touch screen of an automated machine, which is currently and widely installed and operated, thereby having a high industrial availability.

In addition, the sterilizer according to the present invention contains various user protection measures that can protect a user from UV-C light during sterilization of the surface of the touch screen of the automated machine, thereby securing economic feasibility and safety.

In the present invention, the light source 21 in which the multiple high-power UV-C LEDs are arranged on the longitudinal bar and integrated thereto is utilized, and a gap defined between the light source and the touch screen of the automated machine is optimized. Accordingly, the sterilizer of the present invention allows a sterilization operation to be completed during a short time when a next user approaches the automated machine after a previous user finishes using the automated machine so that the next user does not wait during time required to sterilize the touch screen, thereby minimizing transaction time for sterilizing and maximizing sterilization efficiency.

Other effects of the sterilizer according to the present invention will be described in more detail in the detailed description of the invention described below.

BRIEF DESCRIPTION OF THE DRAWINGS

The above and other objects, features, and other advantages of the present invention will be more clearly understood from the following detailed description when taken in conjunction with the accompanying drawings, in which.

DETAILED DESCRIPTION OF THE INVENTION

Hereinafter, the present invention will be described in detail with reference to the accompanying drawings.

The present invention may be variously changed and have various forms, and an embodiment of the present invention will be described in detail hereinafter. However, this is not intended to limit the present invention to a specific disclosure form. Accordingly, it should be understood that the present invention includes all modifications, equivalents, or substitutions included in the spirit and scope of the present invention.

In addition, in each drawing, the size or thickness of each component is expressed to be exaggeratedly large (or thick) or small (or thin) or to have a simple form in consideration of the convenience of understanding. However, the protection scope of the present invention should not be interpreted to be limited thereto.

Terms used herein are only used to describe the specific embodiment (an aspect of the embodiment), and is not intended to limit the present invention. Singular expressions include plural expressions unless the context clearly indicates otherwise. It should be understood that terms such as "comprise" or "include" used herein specify the presence of features, steps, operations, components, or the combination thereof, but do not preclude the presence or addition of one or more other features, steps, operations, components, or the combination thereof.

Unless otherwise defined, all terms used herein, including technical or scientific terms, have the same meaning as commonly understood by those skilled in the art to which the present invention belongs. Terms defined in a commonly used dictionary should be interpreted as having meanings consistent with meanings in the context of related technologies, and should not be interpreted as ideal or excessively formal meanings unless explicitly defined in the present application.

Figure 1:
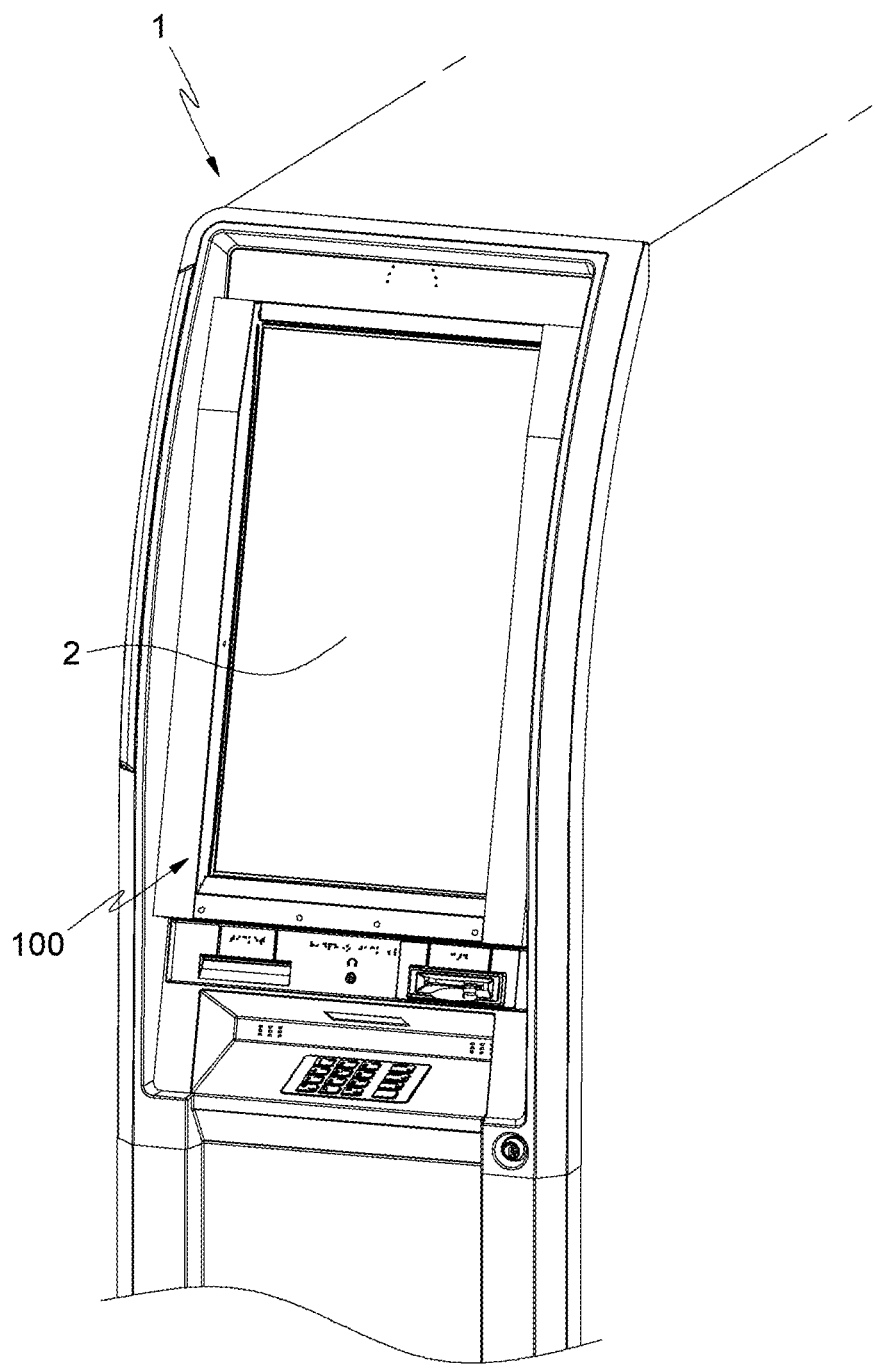
FIG. 1 is a perspective view illustrating a sterilizer according to an embodiment of the present invention attached to a touch screen of an automated machine.
Figure 2:
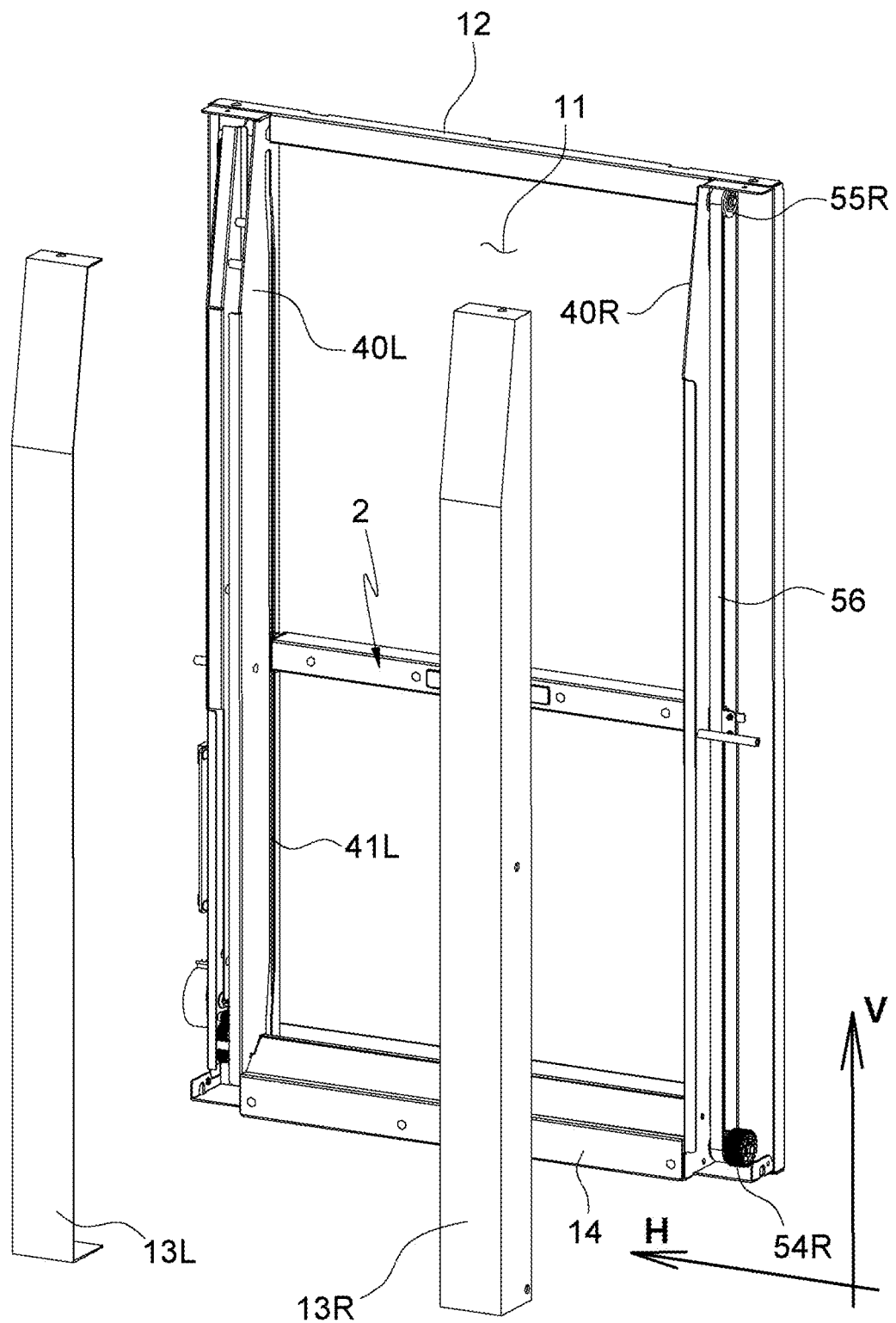
FIG. 2 is an enlarged perspective view illustrating only the sterilizer according to the embodiment of the present invention of FIG. 1 separated from the automated machine.

FIG. 1 is a perspective view illustrating a sterilizer according to an embodiment of the present invention attached to a touch screen of an automated machine, and FIG. 2 is an enlarged perspective view illustrating only the sterilizer according to the embodiment of the present invention of FIG. 1 separated from the automated machine.

The present invention relates to a sterilizer attachable to the bezel of a touch screen of an automated device (an ATM, a kiosk, or a vending machine, etc.) currently in use. Particularly, as illustrated in FIGS. 1 and 2, the present invention relates to the sterilizer, wherein a surface of the touch screen of the automated machine is sterilized while a moving UV bar 20 having a light source, in which multiple LEDs emitting UV-C are arranged, is vertically moved by the driving means.

Particularly, since the touch screen of the automated machine is very large in area, a conventional sterilizer sterilizing the touch screen by moving a moving bar having a light source takes much time to sterilize the entire surface of the touch screen, and has difficulty in being commercialized due to discomfort of a next user being required to wait for a long time after the use of the touch screen by a user. However, in the sterilizer of the present invention, the light source 21 in which multiple high-power UV-C LEDs are integrated to a longitudinal bar moves rapidly, and thus can sterilize the entire area of the touch screen having a large area to be sterilized within a short time.

Figure 3:
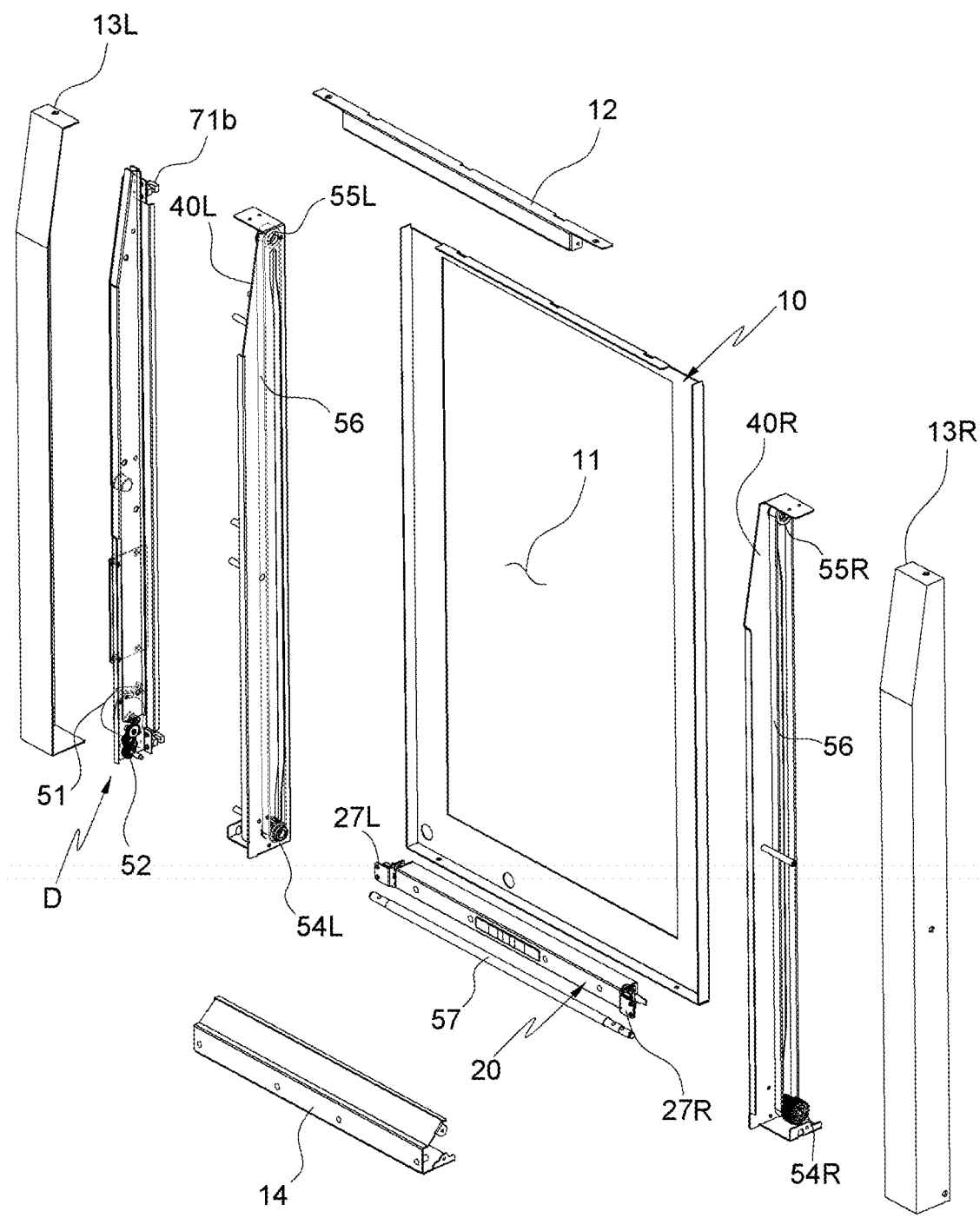
FIG. 3 is an exploded perspective view illustrating the structure of the sterilizer according to the embodiment of the present invention.

FIG. 3 is an exploded perspective view illustrating the overall structure of the sterilizer according to the embodiment of the present invention.

In the UV-C sterilizer according to the present invention, an open portion 11 is provided in the center of a base plate 10 so that the touch screen 2 of the automated machine 1 is exposed through the open portion 11, and a drive source, the driving means, and a connecting rotation shaft are arranged inside vertical covers 13L and 13R at opposite sides of the open portion 11 relative thereto and a horizontal cover 14 above or under the open portion 11.

The base plate 10 of the sterilizer according to the present invention is a component which is in close contact with or attached to the bezel of the touch screen of the automated machine which is being operated, and also functions to securely support the covers 13L, 13R, and 14 and left and right vertical frames 40L and 40R described hereinafter.

Figure 4:
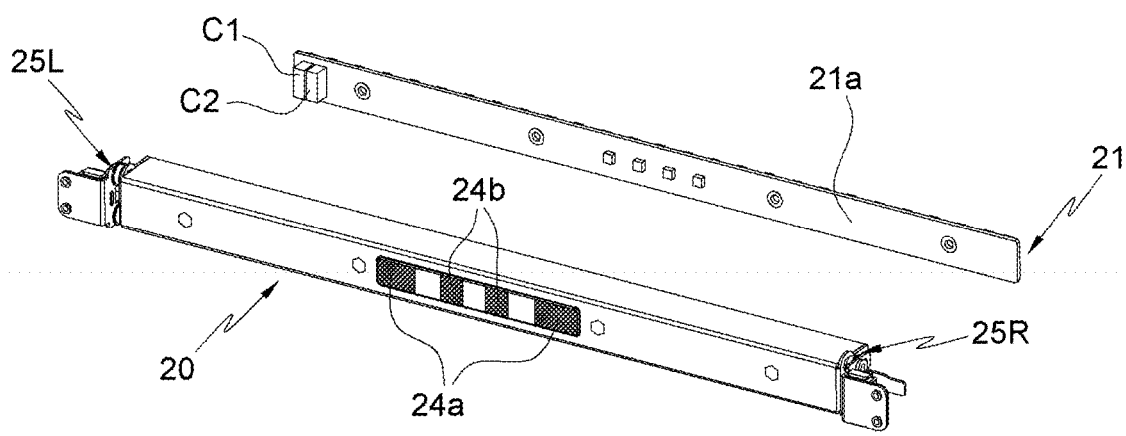
FIG. 4 and FIG. 5 are perspective views illustrating a moving UV bar composed of a light source in which the multiple high-power UV-C LEDs of the present invention are arranged on a longitudinal bar and integrated thereto, and a protection cover protecting the light source.
Figure 5:
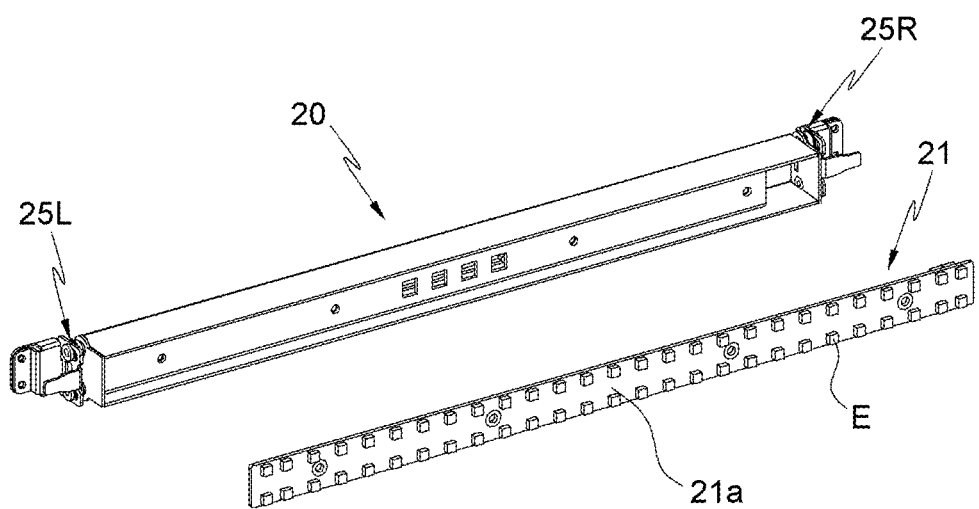
Figure 6:
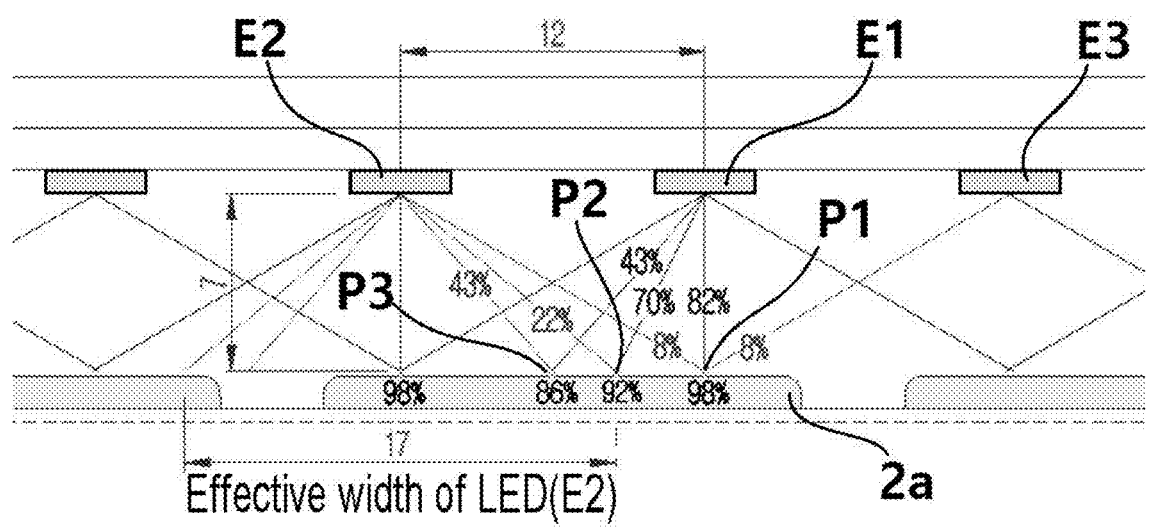
FIG. 6 is a view illustrating the interrelationship of a distance between the surface of a sterilization target and each LED, and an interval between two LEDs adjacent to each other.

FIG. 4 and FIG. 5 are perspective views illustrating the moving UV bar 20 composed of the light source 21 in which the multiple high-power UV-C LEDs are arranged on longitudinal bar and integrated thereto, and a protection cover 22 protecting a user by blocking the light source 21 from the user and dissipating heat generated by LED, and FIG. 6 is a view illustrating the interrelationship of a distance between the surface of a sterilization target and each LED, and an interval between two LEDs adjacent to each other. In FIGS. 4 and 5, a reference numeral C1 refers to a cable socket for power supply, and a reference numeral C2 refers to a cable socket for control signal transmission.

As illustrated in FIGS. 4 and 5, rollers 25L and 25R are coupled to the left and right opposite ends of the moving UV bar 20, respectively.

The left and right rollers 25L and 25R are fitted to slots 41L and 41R, respectively, formed in the vertical frames 40L and 40R, so that the moving UV bar 20 can be stably moved without shaking at the same speeds at the left and right ends thereof. The left and right vertical frames 40L and 40R having the slots 41L and 41R are vertically coupled to the opposite sides of the base plate 10, respectively.

The rollers 25L and 25R at opposite ends (left and right ends) of the moving UV bar 20 may include one or two rollers 25La and 25Lb, and 25Ra and 25Rb, respectively.

In the UV-C LED according to the exemplary embodiment of the present invention, the UV-C LED emitting the light of a wavelength of 265 to 280 nm is applied in consideration of price, sterilization effect, and power consumption, etc. In order to solve the human-toxic problem of UV-C, safety measures described below are applied to the present invention.

The radiant flux of light is inversely proportional to the square of a distance between the surface of a sterilization target and an LED light source, so sterilization efficiency is better as this distance is closer. However, as the distance is closer, the irradiation area of light decreases proportionally. Accordingly, as illustrated in FIG. 6, the distance between the surface of a sterilization target and the LED light source, the interval between the LEDs, and the average arrival rate of UV-C at a specific point on the surface of a sterilization target, etc. are required to be considered.

In the embodiment illustrated in FIG. 6, an interval between UV-C LEDs E1 and E2 adjacent to each other is set to be 12 mm, and a distance between the surface of a sterilization target 2a and the LED E1 is set to be 7 mm.

As illustrated in FIG. 6, the arrival rates of UV-C at points P1, P2, and P3 are 98%, 92%, and 86%, respectively (an average arrival rate 92%), and an effective scan distance in which sterilization effect can be achieved by one LED is calculated to be about 17 mm. If time required to obtain the sterilization efficiency of 99% by one LED is 30 seconds, total time required to sterilize the touch screen having a total movement length of 68 mm is calculated in the following equation: 30 seconds×68 mm/17 mm=120 seconds.

If the number of LEDs is doubled and arranged in two rows, time required for sterilization can be shortened in half.

Accordingly, the distance between the surface of a sterilization target and the LED light source, the setting of the interval between the LEDs in consideration of the average arrival rate of UV-C at the surface of a sterilization target, and the required transaction time for sterilizing are comprehensively considered, thereby minimizing the transaction time for sterilizing and maximizing the sterilization efficiency so that a next user does not wait for the time required for sterilization after a previous user finishes using the automated machine.

Figure 7:
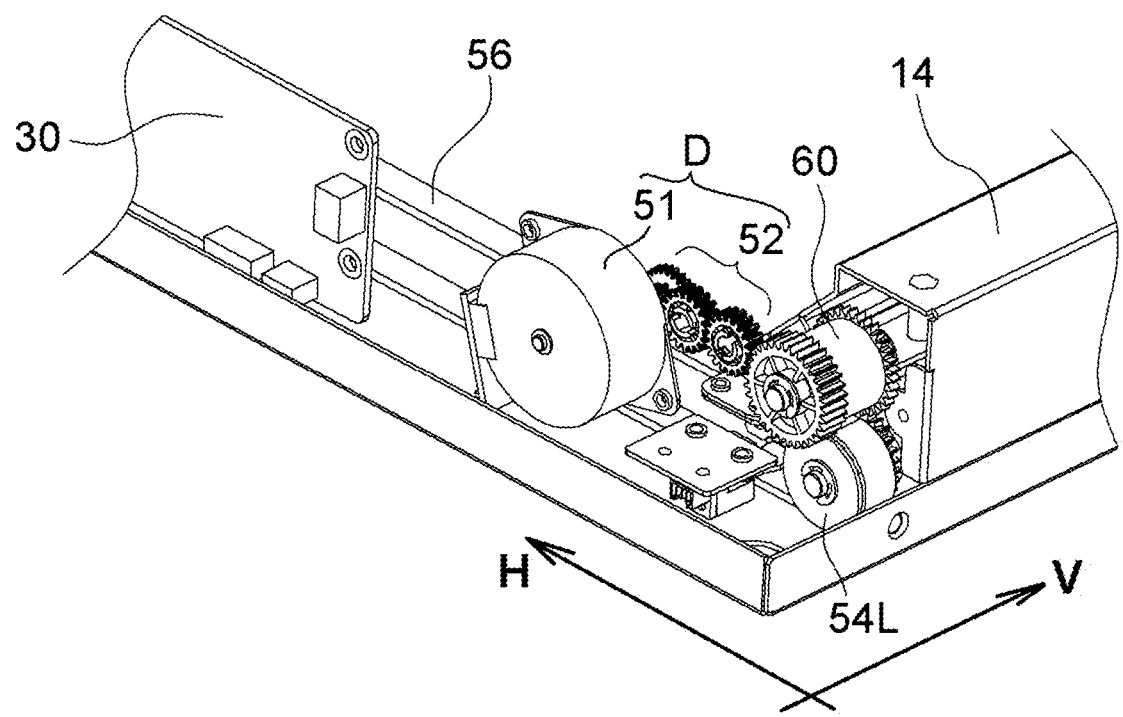
FIG. 7 is a view illustrating the interrelationship of a distance between the surface of a sterilization target and each LED, and an interval between LEDs.
Figure 8:
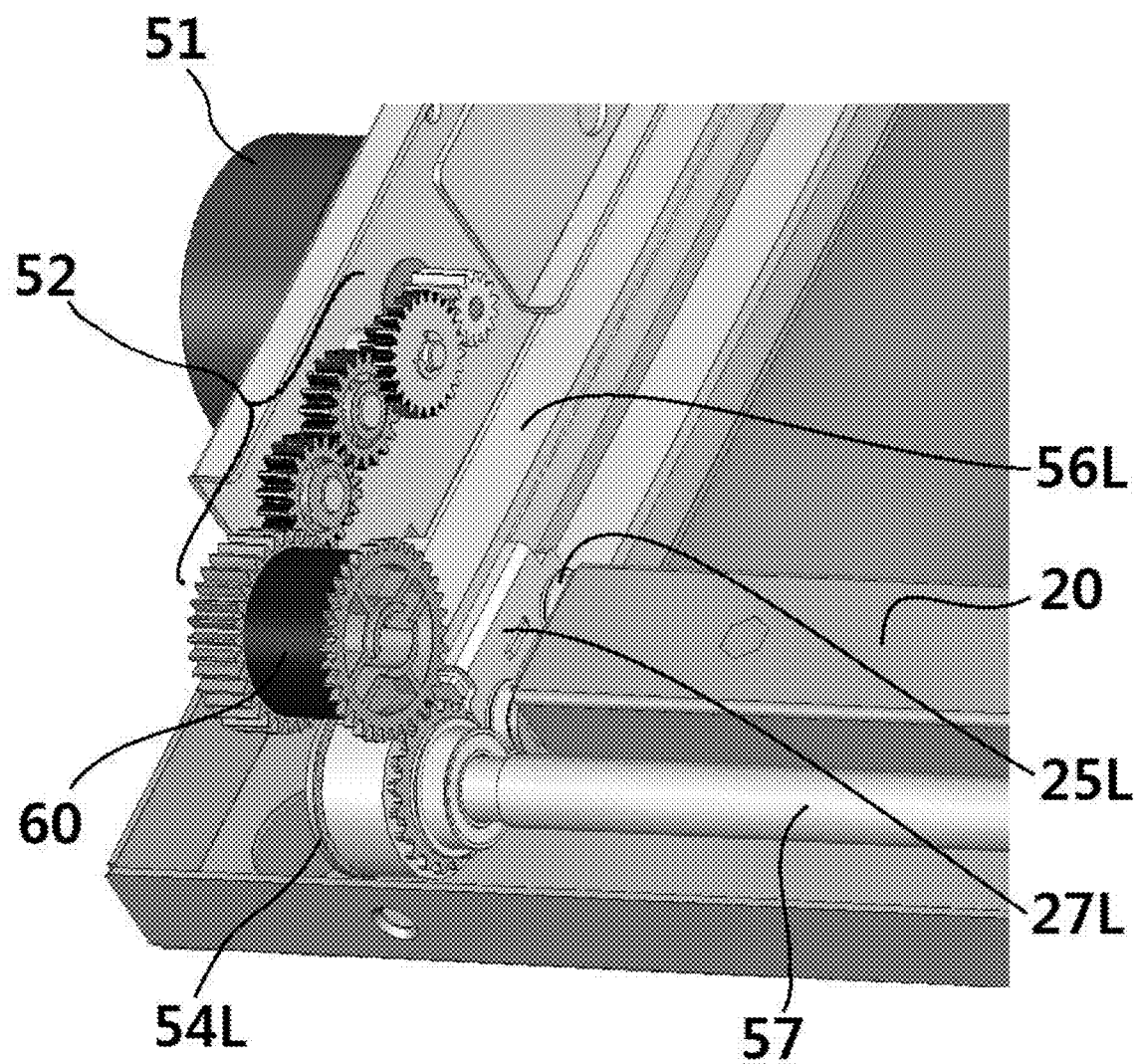
FIGS. 8 and 9 are perspective views illustrating a portion of the driving means of the sterilizer according to the embodiment of the present invention.
Figure 9:
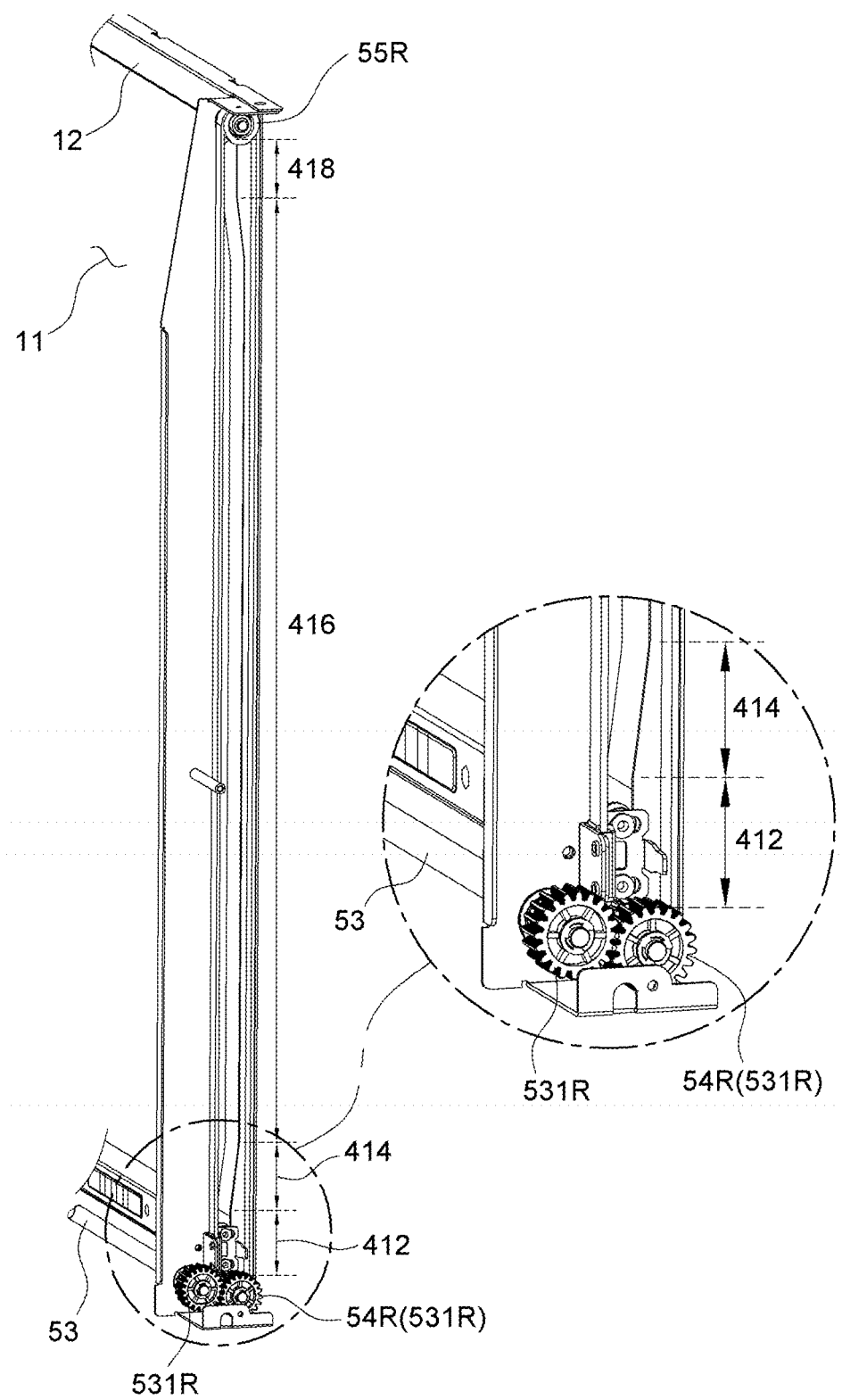
Figure 10:
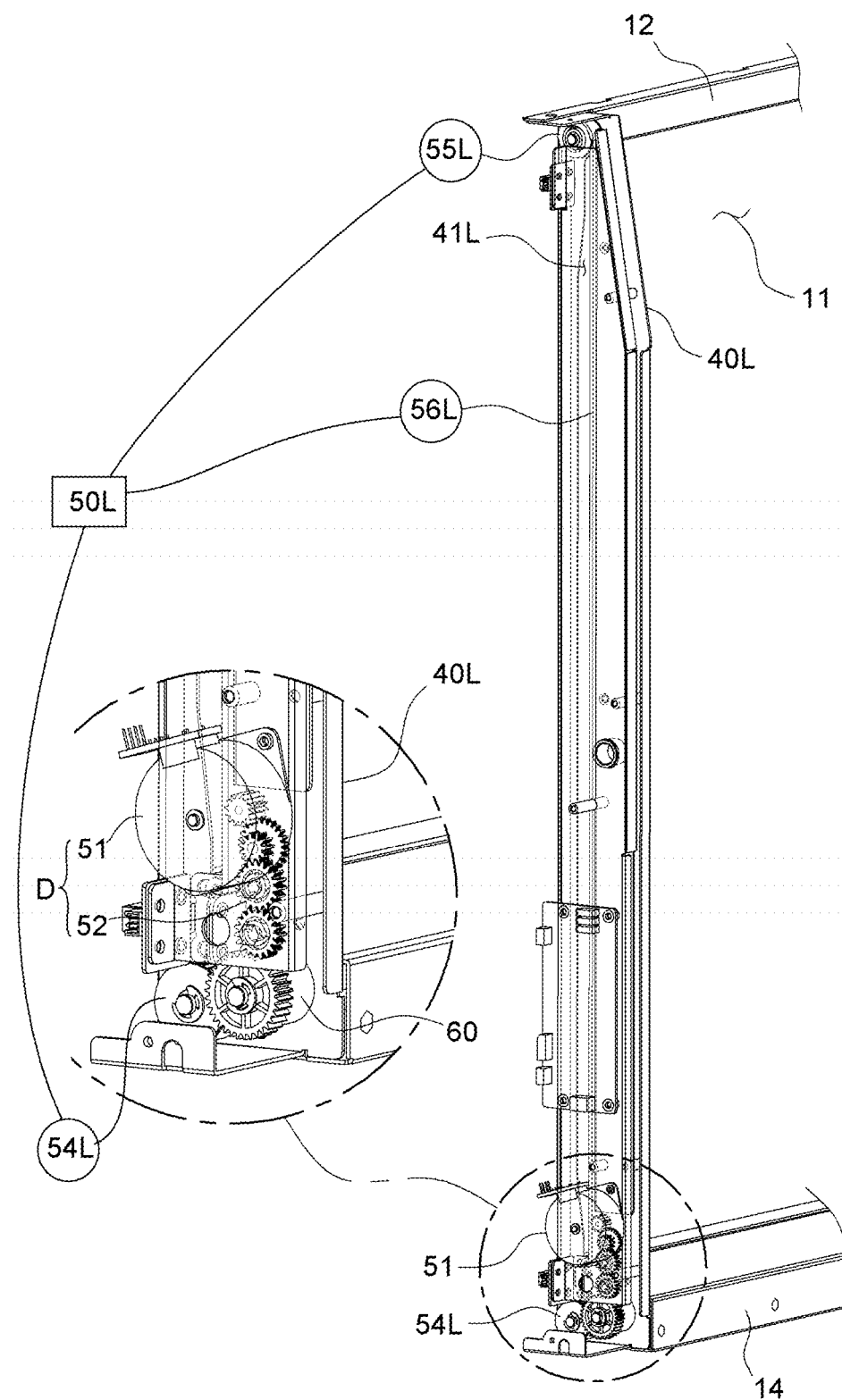
FIG. 10 is a perspective view illustrating a portion of a driving means of a sterilizer according to another embodiment of the present invention.

The embodiment of the driving means driving the moving UV bar 20 provided with the UV-C light source is illustrated in FIGS. 7 and 8, and a driving means illustrated in FIGS. 9 and 10 is illustrated as a modified embodiment of the drive means according to the embodiment of the present invention.

Each driving means as the embodiment and the modified embodiment of the present invention is configured to be compactly arranged inside space defined by the covers 13L, 13R, and 14 and the base plate 10.

The drive source D applied to the sterilizer of the present invention includes a drive motor 51, and a group of electric gears 52, which are provided at a left side relative to the open portion 11 of the base plate 10, wherein the electric gears convert the rotational speed of the drive motor 51 to an appropriate gear ratio and, directly or through an ordinary power transmission means, transmit the appropriate gear ratio to drive pulleys 54L and 54R which are described below.

The driving means according to the embodiment illustrated in FIGS. 7 and 8 is configured to directly transmit a rotational force of the drive source provided inside the left vertical cover to the left drive pulley 54L. The left drive pulley 54L and the right drive pulley 54R are rotated simultaneously by the connecting rotation shaft 57. A reference numeral 60 of FIGS. 7 and 8 refers to a torque limiter, and the specific function of the torque limiter is described in detail below.

The driving means according to the modified embodiment illustrated in FIGS. 9 and 10 includes a power transmission shaft 53 arranged in a horizontal direction, and the rotational force of the drive source provided inside the left vertical cover is transmitted to the right drive pulley 54R by the power transmission shaft 53. The right drive pulley 54R is configured to simultaneously rotate the left drive pulley 54L by the connecting rotation shaft 57. A reference numeral 531R of FIG. 9, which is not described, refers to a right connection gear transmitting the rotational force of the right drive pulley 54R to the power transmission shaft 53. Although not shown in FIG. 10, a left connecting gear or a component equivalent thereto, which transmits the rotational force of the power transmission shaft 53 to the left drive pulley 54L, is naturally required.

The driving means applied to the sterilizer of the present invention is configured to be commonly applied to the embodiment and the modified embodiment, and includes the left and right rollers 25L and 25R rotatably coupled to the opposite ends of the moving UV bar 20; the left and right vertical frames 40L and 40R having the slots 41L and 41R provided, respectively, therein, the slots of the frames guiding the rollers 25L and 25R, and vertically coupled to the opposite sides of the base plate, respectively; the left and right drive pulleys 54L and 54R rotatably coupled to the left and right vertical frames 40L and 40R, respectively, and rotated by receiving the rotational force of the drive motor 51 located at a side; the connecting rotation shaft 57 synchronizing rotational speeds and phases of the left and right drive pulleys 54L and 54R; driven pulleys 55L and 55R corresponding to the left and right drive pulleys 54L and 54R, respectively; left and right timing belts 56L and 56R rotated by being connected to the drive pulleys 54L and 54R and the driven pulleys 55L and 55R; and coupling members 27L and 27R coupling the left and right opposite ends of the moving UV bar 20 to the left and right timing belts 56L and 56R, respectively.

As illustrated in FIGS. 2, 7, 11, and 13, a direction of an arrow V is referred to as an upside; a direction opposite thereto is referred to as a downside; a direction of an arrow H is referred to as a left side; and a direction opposite thereto is referred to as a right side.

The sterilizer 100 according to the present invention is one of many ways to protect a user from UV-C light while sterilizing the touch screen of the automated machine, and provides a solution for maximally securing the durability and mobile stability of the moving UV bar 20.

To make the driving means compact and to synchronize the rotational force, rotational speed, and phase of each of the left and right drive pulleys 54L and 54R, one drive motor is preferably used, and the connecting rotation shaft transmitting the driving force of the drive motor located at a side to a driving means located at a side opposite thereto is required.

In FIGS. 3 and 8, and FIGS. 11 to 13, a reference numeral 57 refers to the connecting rotation shaft transmitting the rotational force and the rotational speed of the drive pulley 54La of a side driven by the drive motor 51 to the drive pulley 54Ra of a side opposite thereto in synchronization with each other.

In the embodiment of the present invention, although it is shown that the connecting rotation shaft 57 is installed in a horizontal direction at a side under the open portion 11, and is protected by the horizontal cover 14, the connecting rotation shaft 57 may be configured to be installed in a horizontal direction at a side above the open portion 11, and to be protected by the horizontal cover 14.

As an important solution for protecting a user from UV-C light during the sterilization of the touch screen of the automated machine, the sterilizer according to the present invention includes the moving UV bar 20 composed of the light source 21 in which the multiple high-power UV-C LEDs are arranged at predetermined intervals on the longitudinal bar and integrated thereto, and the protection cover 22 preventing the light of the light source 21 from being emitted to directions other than a direction toward the surface of the touch screen. A gap defined between a lower edge 222 of the protection cover 22 and the surface of the touch screen is configured to be smaller than the thickness of the fingers of a user.

Considering that the minimum finger thickness of an ordinary user manipulating the touch screen of the automated machine is greater than 4 mm, in the present invention, the gap defined between the lower edge 222 of the protection cover 22 and the surface of the touch screen is configured to be smaller than 4 mm to protect the finger of a user from UV-C light. In the sterilizer according to the embodiment of the present invention, the gap defined between the lower edge 222 of the protection cover 22 and the surface of the touch screen is preferably maintained to be 2 to 3 mm. That is, as the exemplary embodiment of the present invention, the gap defined between the lower edge 222 of the protection cover 22 and the surface of the touch screen is 3 mm or less.

Furthermore, in the sterilizer according to the exemplary embodiment of the present invention, the moving UV bar 20 can move in directions away from and toward the surface of the touch screen while moving up and down.

That is, the surface of a sterilization target and a center line of each of the left and right slots 41L and 41R are configured to maintain a constant distance therebetween, and an inclined section 414 is provided in the slot of a position corresponding to a position at which the height of the surface of a sterilization target changes, so that the moving UV bar 20 moves in the directions away from and toward the surface of a sterilization target while the moving UV bar 20 moves up and down along the surface of a sterilization target.

Figure 11:
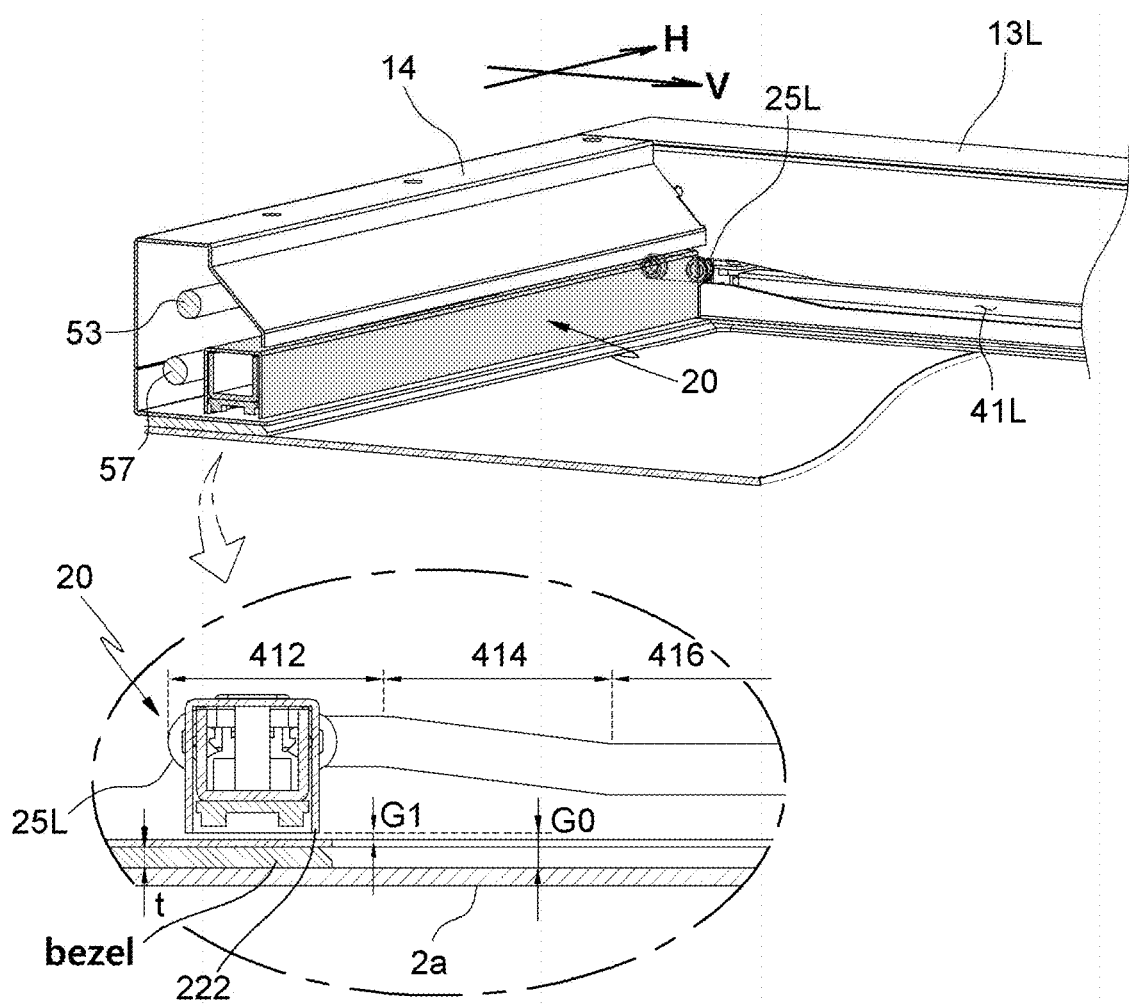
FIGS. 11 to 13 are partial sectional views and partial perspective views illustrating the change of a gap defined between the lower edge of the protection cover and the surface of a sterilization target while the moving UV bar of the present invention is moving along slots.
Figure 12:
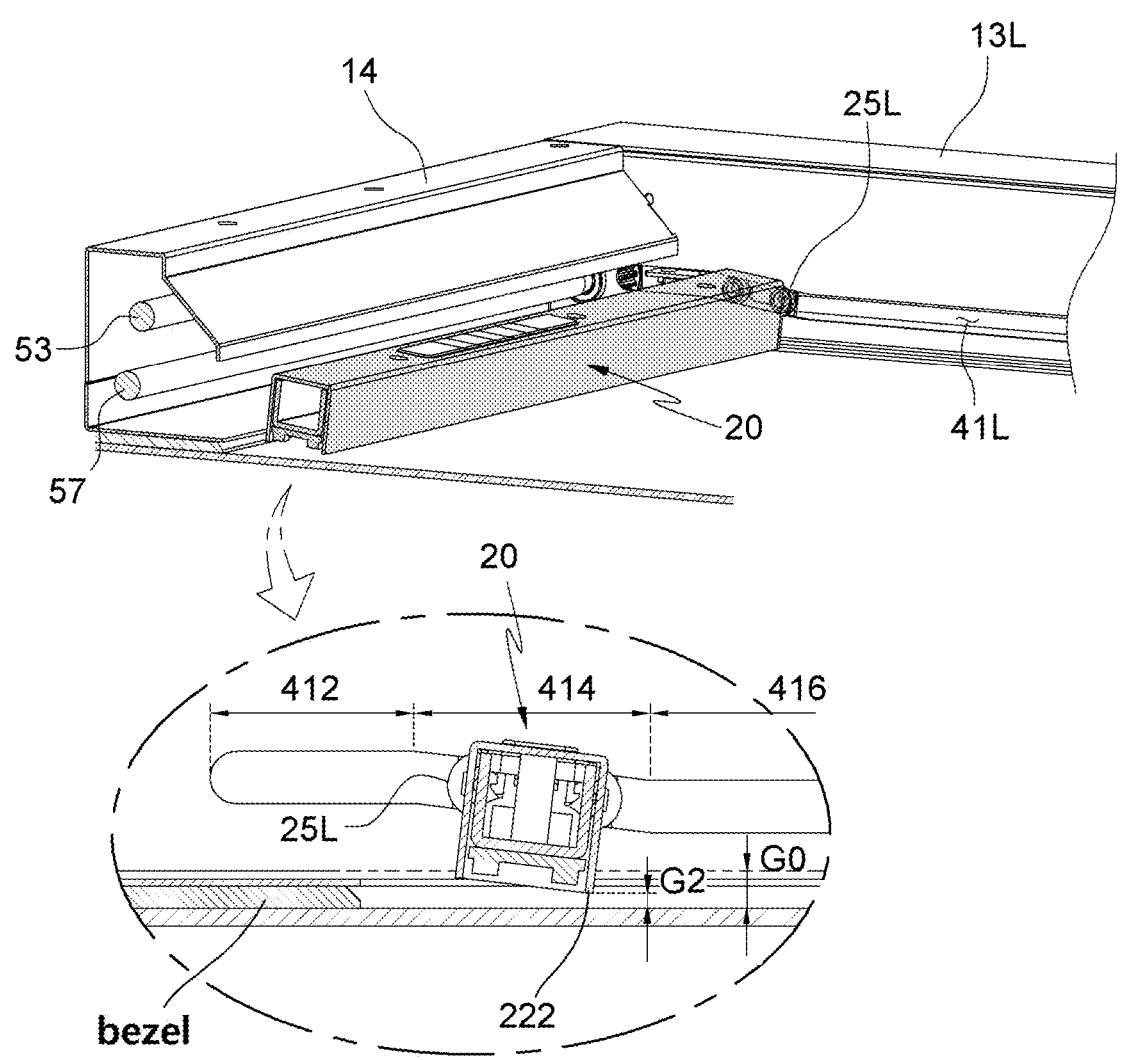
Figure 13:
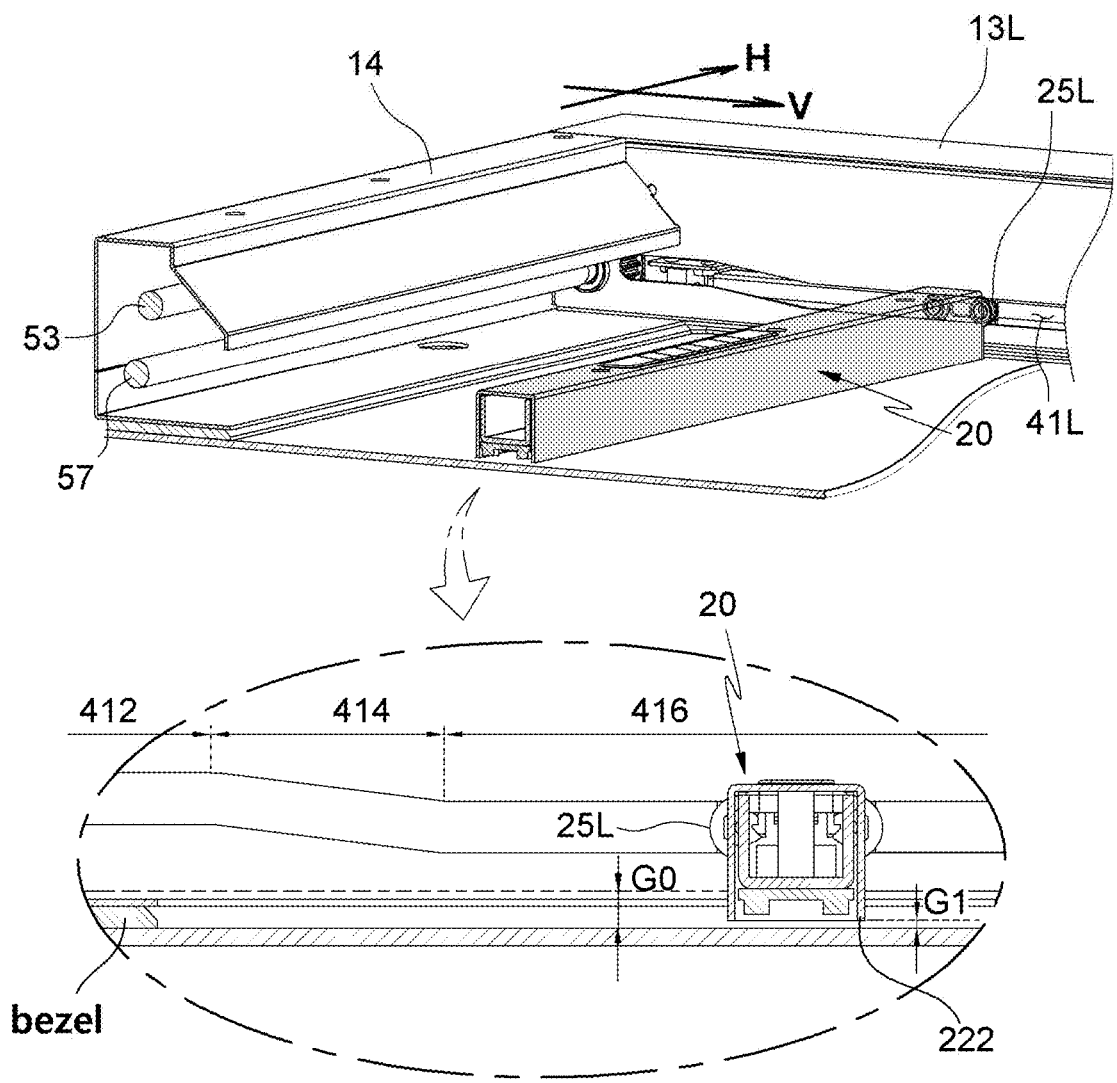

FIGS. 11 to 13 are partial sectional views and partial perspective views illustrating the change of the gap defined between the lower edge 222 of the protection cover 22 and the surface of a sterilization target while the moving UV bar 20 of the present invention is moving along the slots 41L and 41R.

As described above, since the present invention is intended to propose the UV-C sterilizer attached to the bezel of the touch screen of the automated machine, the home position of the moving UV bar 20 is preferably located on the bezel of the touch screen. If the home position of the moving UV bar 20 is located at the edge of the touch screen, the moving UV bar 20 partially covers the touch screen, which is very likely to make a user's input operation uncomfortable or impossible.

For this reason, in the sterilizer of the present invention, the home position of the moving UV bar 20 is located on the bezel of the touch screen. FIG. 11 illustrates a state in which the moving UV bar 20 of the sterilizer of the present invention is located at the home position. As illustrated in FIG. 11, when the moving UV bar 20 is located at the home position, the gap G1 between the surface of the bezel of the touch screen and the lower edge 222 of the protection cover 22 maintains 2 to 3 mm which is a gap safe to a user.

FIG. 12 illustrates a state in which the moving UV bar 20 is outside the bezel of the touch screen after the operation of the moving UV bar 20 starts. Each of the left and right slots 41L and 41R according to the present invention has the inclined section 414 provided at a position corresponding to a position (that is, a boundary of the bezel of the touch screen) at which the height of the surface of a sterilization target changes. That is, in the left and right slots 41L and 41R according to the present invention, "a home section 412" is provided at a position at which the moving UV bar 20 stays at the home position, and "the inclined section 414" is provided at the position corresponding to the position (that is, the boundary of the bezel of the touch screen) at which the height of the surface of a sterilization target changes.

As illustrated in FIG. 12, the moving UV bar 20 moving along the inclined section starts the movement of approaching the surface of a sterilization target and can maintain a gap G2 between the surface of the touch screen and the lower edge 222 of the protection cover 22 within an allowable limit value.

If there is no inclined section in the slot, the moving UV bar 20 still moves rectilinearly without approaching the surface of a sterilization target. Accordingly, the gap G0 defined between the surface of the touch screen and the lower edge 222 of the protection cover 22 is the combined gap of the thickness t of the bezel of the touch screen and the initial gap G1, which results in a large gap. When the gap increases in this way, a user may be injured by the UV-C light due to the user's abnormal action (the action of pushing the finger into the gap).

The degree of inclination of the inclined section 414 may be appropriately designed in consideration of the change of the height of the surface of a sterilization target within the range in which the rolling operation of the rollers provided at the opposite ends of the moving UV bar 20 is not interfered with.

FIG. 13 illustrates a section (hereinafter, referred to as a "flat section 416") in which the moving UV bar 20 passing through the inclined section moves rectilinearly along a flat surface of the touch screen.

The value of a gap between the center line of the slot in the flat section 416 and the center line of the slot in the home section 412 is preferably configured to be the same as height difference (the thickness t of the bezel of the touch screen in the case of an example shown in FIGS. 11 to 13) between the surface of a sterilization target in the flat section 416 and the surface of a sterilization target in the home section 412.

By configuring in this way, the gap G1 defined between the surface of the touch screen and the lower edge 222 of the protection cover 22 while the moving UV bar 20 is moving in the flat section 416 can be maintained to be the same as the gap G1 defined in the home section 412.

If the surface of a sterilization target has multiple height differences (for example, in the case that a bezel dividing into an upper portion and a lower portion of the touch screen is located in the middle of the touch screen), the inclined section and flat section of the slot according to the present invention are configured in plural so that the same purpose and operational effect can be obtained.

To transmit the specific position (for example, a home position, a middle position, a return position, etc.) of the moving UV bar 20 to a controller, at least a sensor 71a, 71b is provided at the left side or the right side so that the position of the moving UV bar 20 can be checked.

The sterilizer according to the present invention further includes a torque limiter 60 as an important solution of protecting a user from UV-C light and preventing the sterilizer from being damaged due to an abnormal manipulation of a user during the sterilization of the touch screen of the automated machine, the torque limiter being provided at an intermediate position of a power transmission system by which the rotational force is transmitted from the drive motor 51 to the drive pulleys 54La and 54Ra.

When the movement of the moving UV bar 20 is restricted by the impact of a user while the moving UV bar 20 performs UV-C sterilization during the vertical movement, the moving UV bar 20 stops moving, and the drive motor 51 continues to rotate. In this case, the drive motor 51 or the power transmission system is overloaded, so a portion of a mechanical structure may be damaged.

When such a problem occurs, the torque limiter 60 functions to limit the rotational force of the drive motor 51 from being transmitted to the drive pulleys any more. Accordingly, in the sterilizer of the present invention having the torque limiter 60, even when the movement of the moving UV bar 20 is restricted by a user while moving (during UV-C sterilization), a mechanical structure can be prevented from being damaged, and further, a signal can be transmitted to the controller such that the moving UV bar 20 is returned to a home position or is moved to a temporary position when an operational malfunction is determined to occur by a user so as to stop the operation of the moving UV bar 20.

To protect a user, the sterilizer according to the embodiment of the present invention may further include a controller receiving information on whether or not a user is in front of the automated machine from the automated machine, and controlling such that the sterilizer is operated when there is no user.

The controller may be configured to control the sterilizer such that an electric current is applied to the UV-C LEDs only when each part of a driving mechanism, a control board, and a software is recognized to be in a normal state. Accordingly, the controller is configured to apply an electric current to the UV-C LEDs only when each part of the sterilizer of the present invention is in a normal state, and to cut the application of an electric current to the UV-C LEDs when any one part of sterilizer is not in the normal state so that the safety of a user can be improved.

The controller may be configured to control the sterilizer such that a status result value of the sterilizer is transmitted to the automated machine after checking whether each part thereof is in a normal state such that information on whether the sterilizer is operated or the maintenance of the sterilizer can be maintained inside the operating system of the entirety of the automated machine.

In the sterilizer according to the exemplary embodiment of the present invention, as illustrated in FIGS. 4 and 5, the operation state of the sterilizer is preferably displayed for a user on the upper surface of the protection cover 22 of the moving UV bar 20 by two color LEDs 24 to inform the user that a sterilization operation is in progress so that the user can wait until the start of use of the automated machine.

In addition, the sterilizer according to the exemplary embodiment of the present invention is provided with a purple-colored LED 24b in parallel with the UV-C LEDs, and allows a user who cannot see the light of a UV-C wavelength to recognize the emission of UV-C light through the light of the above-described purple-colored LED so that the user is careful.

The sterilizer according to the present invention described so far is specifically described to have various solutions applied thereto to prevent UV-C light from being harmful to users.

So far, the sterilizer according to the present invention has been described by focusing on the exemplary embodiment, but the sterilizer according to the present invention may be modified in various forms.

What is claimed is:

1. A sterilizer attachable to a touch screen of an automated machine, the sterilizer sterilizing a surface of the touch screen of the automated machine while vertically moving a moving UV bar having a UV light source by using a drive source and a driving means, the sterilizer comprising:

a moving UV bar having a light source in which multiple high-power UV-C LEDs are arranged at predetermined intervals on a longitudinal bar and integrated thereto, and a protection cover preventing light of the light source from being emitted in directions other than a direction toward a surface of a touch screen;

a base plate having an open portion corresponding to the touch screen of an automated machine and attachable to a bezel of the touch screen;

a horizontal cover provided in a horizontal direction above or under the open portion, and a vertical cover provided at each of opposite sides of the open portion to protect the drive source and a driving means; and the drive source and the driving means configured to be compactly arranged inside a space defined by the covers and the base plate, wherein the moving UV bar is configured to move in directions away from and toward a surface of a sterilization target by corresponding to change of a height of the surface of the sterilization target while the moving UV bar moves up and down along the surface of the sterilization target, so that a gap defined between a lower edge of the protection cover and the surface of the sterilization target is maintained to be constant.

2. The sterilizer of claim 1, wherein the driving means comprises:

left and right rollers rotatably coupled to opposite ends of the moving UV bar, and left and right vertical frames having a slot provided in each of the vertical frames, the slots of the frames guiding the rollers, and vertically coupled to opposite sides of the base plate, respectively, wherein the surface of the sterilization target and a center line of each of the left and right slots are configured to maintain a constant distance therebetween, and an inclined section is provided in a slot of a position corresponding to a position at which the height of the surface of the sterilization target changes, so that the moving UV bar moves in the directions away from and toward the surface of the sterilization target while the moving UV bar moves up and down along the surface of the sterilization target.

3. The sterilizer of claim 2, further comprising:

a torque limiter provided at an intermediate position of a power transmission system by which a rotational force is transmitted from a drive motor to drive pulleys, the torque limiter preventing damage of components of the automated machine when the movement of the moving UV bar is restricted by impact of a user while the moving UV bar performs UV-C sterilization during vertical movement thereof, and controlling so that the moving UV bar is returned to an original position thereof or is moved to a temporary position after the user determines that an operational malfunction occurs when the moving UV bar does not reach a sensor at a specific position by a predetermined time.

4. The sterilizer of claim 2, further comprising:

a controller controlling operations of the driving means and the UV-C LEDs, wherein the controller receives information on whether or not a user is in front of the automated machine from the automated machine, and controls such that an electric current is applied to the driving means and the UV-C LEDs when there is no user.

* * * * *